Figure 1:
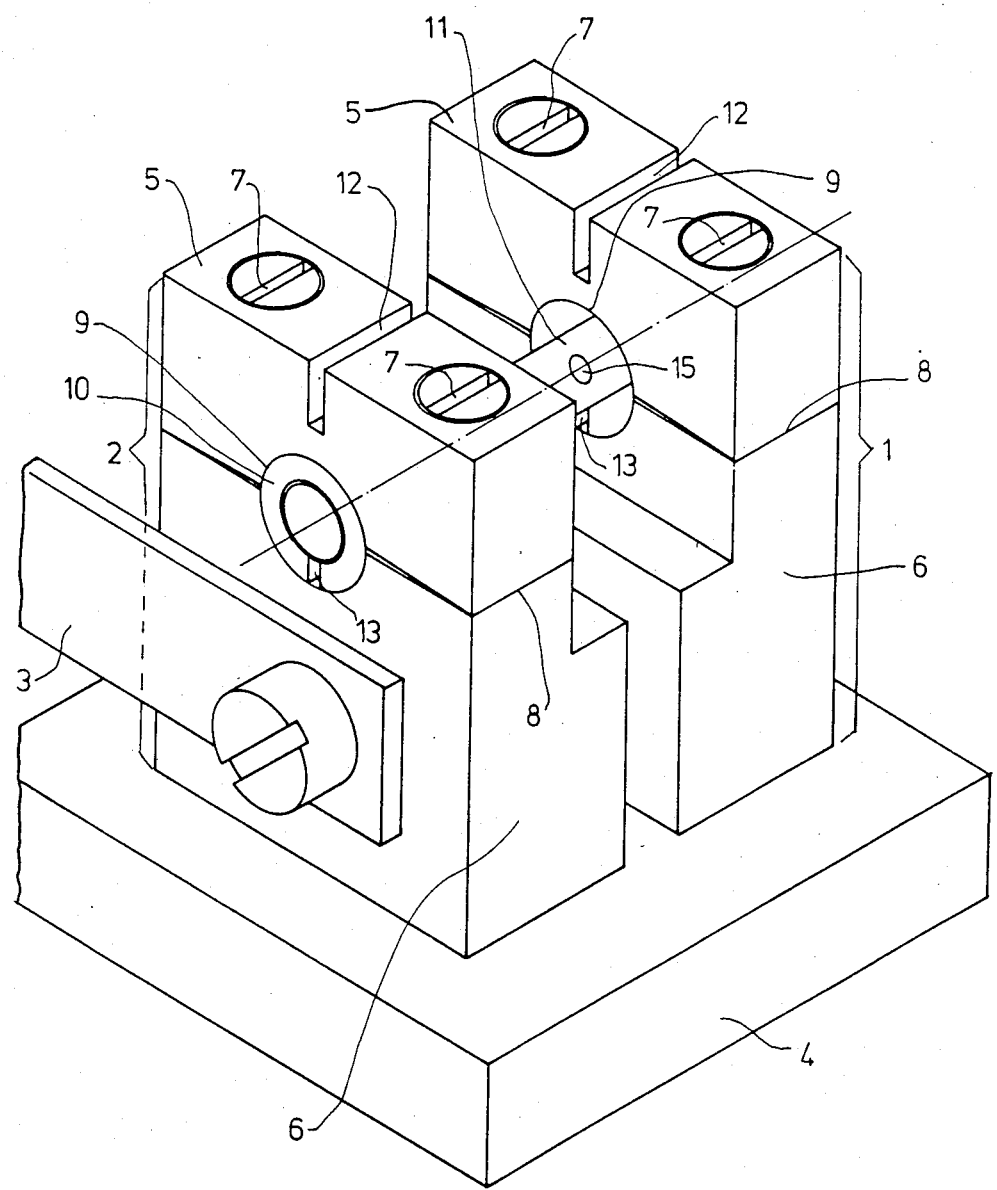

United States Patent [19]

Lersmacher et al.

[11] Patent Number: 4,653,913

[45] Date of Patent: Mar. 31, 1987

[54] HEATING DEVICE FOR AN ATOMIC ABSORPTION SPECTROMETER

[75] Inventors: Bernhard Lersmacher, Aachen; Paul-Heinz Poqué, Würselen, both of Fed. Rep. of Germany; Klaus-Dieter Zimmermann, VW Vaals, Netherlands

[73] Assignee: U.S. Philips Corporation, New York, N.Y.

[21] Appl. No.: 745,737

[22] Filed: Jun. 17, 1985

[30] Foreign Application Priority Data

Jul. 28, 1984 [DE] Fed. Rep. of Germany ....... 3427995

[51] Int. Cl.$^4$ ............................................. G01N 21/74
[52] U.S. Cl. ..................................... 356/312; 356/244
[58] Field of Search ............................... 356/312, 244

[56] References Cited

U.S. PATENT DOCUMENTS 3,873,205 3/1975 Thompson ..................... 356/244 X
3,895,873 7/1975 Dennison et al. .................... 356/312

Primary Examiner—Vincent P. McGraw
Attorney, Agent, or Firm—Paul R. Miller

[57] ABSTRACT

In a heating device for atomic absorption spectrometers with electrothermal excitation of a sample, a tubular body for receiving the sample comprises a radial aperture (15) for introducing the sample at the central part of the tubular body. A pair of contacts (1, 2) can be cooled comprise current supplies (3), each consisting of a detachable upper part (5) and a fixed lower part (6) with the upper part and the lower part being connected together so as to be detachable. Each contact comprises an aperture (9) which is coaxial with the tubular body with the apertures extending partly in the upper part and partly in the lower part of the contacts and holding the ends of the tubular body. Damage and deformations of the contacts are avoided in that the diameters of the apertures (9), with the upper parts (5) laid flush on the lower parts (6), are shorter in the vertical direction than in the horizontal direction. The upper parts (5) of the apertures (9) each have a groove (12) which points upwards and extends parallel to the longitudinal axis of the apertures (9). On each end of the tubular bodies (11) a resilient clamping ring (10) is slid whose inside diameter is smaller than the outside diameter of the tubular body (11) and whose outside diameter corresponds to the apertures of the contacts (1, 2). The clamping ring comprises a vertical slot (13) at the area of the lower part (6). Alternatively instead of the clamping rings the ends of the tubular body (11) optionally comprise flanges (14) at its end and are surrounded by graphite foil.

11 Claims, 3 Drawing Figures

HEATING DEVICE FOR AN ATOMIC ABSORPTION SPECTROMETER

The invention relates to a heating device for an atomic absorption spectrometer with electrothermal excitation of a sample, comprising a tubular body for receiving the sample which can be heated by means of current passage and which body comprises in its central portion a radial aperture for introducing the sample, and a pair of contacts which can be cooled comprise current supplies with each pair consisting of a detachable upper part and a rigidly connected lower part and with the upper part and the lower part being connected together so as to be detachable, each contact comprising an aperture which is coaxial with the tubular body with the apertures extending partly in the upper part and partly in the lower part of the contacts and enclosing ends of the tubular body.

A heating device having contacts each consisting of an upper part and a lower part is shown in FIG. 1 of DE Pat. No. 2,735,467. Details of the construction of such a heating device, but with undivided contacts, are known from DE Pat. No. 2,413,782. It is known from U.S. Pat. No. 3,893,769 to provide a conical clamping ring on the ends of the tubular body and to arrange the clamping rings with the ends of the tubular body in the apertures of undivided contacts.

In atomic absorption spectrometry (AAS) the sample to be analysed traverses a certain temperature-time cycle in the course of which the material of the sample is fully decomposed by thermal dissociation and the components are transferred into the atomic vapour phase. In this step, which is referred to as atomisation, the element to be determined can be detected selectively by means of spectrochemical methods and quantitatively with a very high accuracy. In accordance with the nature of the sample the atomisation step requires temperatures of up to 3000° C. Particularly suitable for this sample preparation are thin-walled, i.e. approximately 1 mm thick, preferably tubular bodies which can be heated by means of current passage, usually of graphite, so-called AAS cuvettes. They fulfil a double function in that they serve simultaneously as a container for the sample which in most of the cases is a few microliters large, and as a resistance element and furnace, respectively, for the electric heating. In accordance with the size and the operating system, electric powers of up to a few kilowatt are required for the heating. The heating currents may reach a few 100 Amperes. The electrical contacts in the heating devices of atomic absorption spectrometers are hence exposed to particularly high loads. This applies even more so since, in addition to high current densities due to the cyclic heating and cooling, during operation strong heating currents also have to be overcome and, due to the interchangeability of the cuvettes, the contacts must be detachable and of the simplest form. The contacts in the heating devices therefore represent real vulnerable points. Defects and damage of the contact materials, which consist, for example, of nickel-plated copper, in the form of permanent plastic deformations at the clamping points of the cuvettes occur in particular. This damage does not only adversely influence the progress of the analysis, it also leads to expensive maintenance and repair work, for example, by replacing parts of the contacts.

It is the object of the invention to avoid such damage and deformations of the contacts and hence to make the heating device more reliable.

According to the invention this object is achieved in that the diameters of the apertures in the contacts, with the upper parts laid flush on the lower parts, are shorter in the vertical direction than in the horizontal direction, that each of the upper parts comprises above the apertures a groove which points upwards and extends parallel to the longitudinal axis of the apertures, and that on the ends of the tubular body a resilient clamping ring is slid having an inside diameter smaller than the outside diameter of the tubular body and having an outside diameter corresponding to the apertures in the contacts and which at the area of the lower part comprises a vertical slot, or that instead of the clamping rings the ends of the tubular body optionally comprise flanges at its ends being surrounded by graphite foil, or alternatively the inner surfaces of the apertures are lined with graphite foil.

Since, with the upper part lying flush on the lower part, the vertical diameter of the aperture formed, i.e. the receiving aperture for the cuvette, is slightly smaller than the horizontal diameter, the aperture has a shape, i.e. a geometry, which deviates slightly from the circular shape. When, after detaching the upper part from the lower part, a circular contacting or clamping ring slid on the ends of the tubular body, i.e. of the cuvette, is laid in the aperture and when the two contact parts are closed, for example by screwing, the upper and lower parts press against the clamping ring and this will generally be a point contact.

The upwardly pointing grooves in the center of the upper parts enable an elastic deformation upon contacting in the sense of a "static fulcrum". This results in a groove between the upper and lower parts which is slightly conical, i.e. widens in the direction towards the aperture.

The slot of the clamping or contacting ring on the cuvette is adjusted vertically and is present in the area of the lower part of the contacts. The result of this arrangement of grooves and slots in cooperation with the forces provided upon contacting is a tangential grip of clamping ring on the one hand and AAS cuvette on the other hand. The result of this is that comparatively poorly transmitting point contacts change into readily transmitting annular, linear contacts.

For a perfect operation of the contacting system according to the invention it is advantageous to keep the tolerances in the dimensions, in particular those of the outside diameters of the clamping rings and the inside measures of the receiving apertures in the contact blocks, very small, i.e. the two above values should correspond, for example, to the fits h6/N6 (according to the ISA-standard).

In the above-described alternative embodiment such a high accuracy of fit may be omitted. For that purpose it is necessary to line the inner surfaces of the receiving apertures with graphite foil.

The diameters of the apertures in the contacts in the vertical direction are preferably 0.4 to 0.6% shorter than in the horizontal direction. Accordingly the inside diameters of the clamping rings preferably are 0.4 to 0.5% smaller than the outside diameter of the tubular body.

Figure 2:
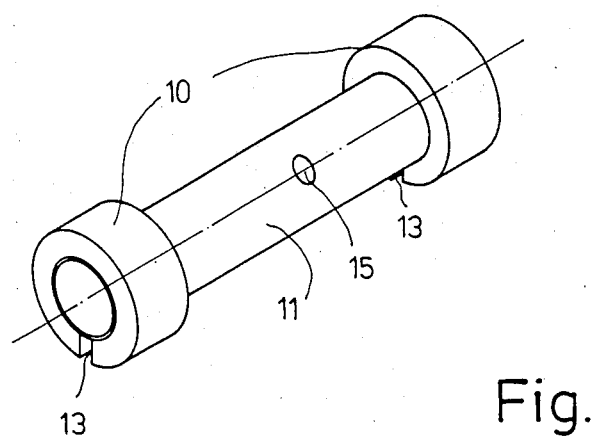
Figure 3:
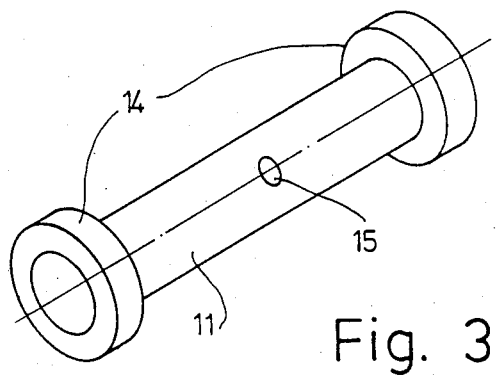

An embodiment of the invention is shown in the drawing and will be described in detail hereinafter. In the drawing FIG. 1 is a perspective view of a heating device and FIGS. 2 and 3 are perspective views of two embodiments of cuvettes for a heating device.

The heating device (FIG. 1) is characterized by several structural and material-bound features which are essential for perfect operation. The main components are two solid blocks 1 and 2 preferably of electrically readily conductive materials, for example of copper, hereinafter also termed contact blocks, which are provided with current supplies 3 and are connected to cooling devices, for example, air cooling or water cooling (not shown). However, other suitable materials for the contact blocks are stainless steel, high-melting-point metals, and graphite. The contact blocks may be coated with corrosion-resistant and surface-finishing protective layers for example of chromium, chromium-nickel, nickel, gold or platinum, and/or with electrically readily conductive, wear-resistant, 2 to 6 μm thick layers of titanium carbide, titanium nitride, carbonitrides or similar materials. The latter layers may be provided at temperatures of approximately 800° C. by means of CVD methods, for example on copper and steel. The contact blocks are mounted either rigidly or movably (for the adjustment of variable distances) on an insulating base plate 4, for example of glass ceramic.

Each contact block consists of a detachable upper part 5 and a rigidly fixed lower part 6. The upper part and the lower part are connected together so as to be detachable, in the present example by simple screw-connections 7. Other possibilities of providing contact-clamping forces—instead of the screw connections used in the present example—are, for example, those which operate with spring systems, mass forces, pneumatic and/or hydraulic systems. The upper part and lower part contact each other without inserted cuvette "sealingly" in a common contact face between upper and lower part. With inserted cuvette on the contrary the contact face is reduced to a contact edge at 8. Both parts of each of the two contact blocks are provided with a substantially semicircular aperture 9 of the same radius.

An essential feature of the invention is that the diameter of the aperture 9, with flush upper parts, is slightly shorter in the vertical direction than in the horizontal direction. This difference is produced in that the aperture which has been drilled circularly symmetrically, with the center in the center of the interface of upper and lower parts, is provided with the interposition of a thin spacer (for example a foil). After removing the spacing member, for example with the thickness δ=50 μm, the difference in diameter ΔD upon combining upper and lower parts is obtained according to the equation $$\Delta D = D_2 - D_1 = \delta (\text{for } D_2 + D_1),$$

wherein $D_1$ is the diameter in the vertical direction, for example 9.950 mm, and $D_2$ is the diameter in the horizontal direction, for example 10.000 mm.

This difference in diameter, i.e. outside diameter of the clamping ring 10 minus inside diameter of the apertures 9 of the contact blocks, must correspond approximately to the tolerances h6/N6 usual in the art. This "uncircularity" of the receiving apertures for the cuvettes 11 enables the close contact of two concave surfaces by means of the grooves 12 provided in the upper parts 5, i.e. the lowest possible hertzian surface pressure, i.e. the lowest possible tensile stresses in materials sensitive to tensile stresses, for example, graphite. This results in a uniform contact pressure which is distributed over the surface in three points. This effect of the uniform distribution of the contact pressure is achieved by the following further characteristic feature:

Two resilient clamping rings 10 are used which are provided with slots 13 at one point of the circumference which after mounting is situated in the area of the lower part 6. The slots 13 should be provided as vertically as possible, so pointing downwards perpendicularly. The inside diameter of the clamping rings is slightly smaller than the outside diameter of the cuvette tube; their outside diameters correspond to the receiving apertures of the contact blocks with tolerances of, for example, h6/N6.

The clamping rings 10 preferably consist of graphite, for example electrographite. Other useful materials for the rings are pyrolytic graphite, vitreous carbon and high-melting-point metals, for example, molybdenum, tungsten, tantalum or the carbides thereof. When the above-given prescriptions are maintained the clamping rings can be slid on the tubular body, i.e. the cuvette, with a slight force fit. Such an arrangement is shown in FIG. 2. The operation of the clamping rings may be described as follows: first they operate in the sense of the already mentioned force distribution by tangential slide. They can absorb or compensate for small expansions or shrinkages dependent on thermal or mechanical stresses. Moreover, the immediate contact of the cuvette which is heated at a high temperature and the comparatively cold contact block is avoided. By suitable choice of the material—for example pyrolytic graphite—and proportioning of the ring, electrical and thermal resistances of the clamping rings can be varied in wide limits and hence the temperature distribution and the thermal balance on the cuvette can be influenced positively. Moreover, the clamping ring construction above all also facilitates axial expansions and contractions of approximately 0.05 to 0.1 mm, as they occur in every analysis cycle as the result of the strong temperature change. The coefficient of thermal expansion of pyrolytic graphite (a known material for AAS curvettes) in the crystallographic ab direction namely is approximately $1 \times 10^{-6}/°C$. With a cuvette length of 30 mm a longitudinal expansion of approximately $30 \times 3000 \times 10^{-6}$ mm equal to approximately 0.1 mm is obtained for a maximum temperature of 3000° C.

A further characteristic detail of the heating device is the groove 12 in each of the upper parts 5 of the contact blocks shown in FIG. 1. The groove permits a hinge-like deformation of the upper part and only thereby permits the above-mentioned close 3-point-contact pressure and an elastic and resilient expansion compensation, respectively, and thereby again permits an optimum clamping force distribution over the circumference of the cuvette. A groove starting at 8 is formed in that the facing surfaces of the upper part and the lower part with closed contacts enclose an angle of approximately 0.14° with the apex of the angle forming the line in which the upper part and the lower part of each contact block contact each other on the outside.

In a modified manner the heating device was also tested on AAS cuvettes with flanges 14 (FIG. 3). Instead of the above-described clamping ring a piece of graphite foil (not shown; trade name, for example, Sigraflex, Papyex, Grafoil) of 0.2 mm thickness, as a contact means between the rigid cuvette ends and the contact members, was laid in the contact recesses in such manner that in the operating condition they firmly enclose the cuvette ends and cuvette flanges, respectively, under the action of the compression pressure of the contacts. The thickness of the foil may vary between 0.1 and 0.5 mm.

The known foil is a product which is manufactured by cold rolling from pretreated natural graphite. Since it relates to pure graphite without additions, the product is free from impurities. Similar to highly oriented pyrolytic graphite, its particularity is an excellent anisotropy of its physical properties which is very favourable in the present application. Moreover said material is plastically deformable. In this respect it behaves as a foil of a ductile metal, for example, lead. The result of this is that in the play of forces the cuvette ends during operation are truly impressed in the foil material and as regards their position thus fix themselves. This is of great advantage for the usually automated injection of the sample solution through the filling holes of the cuvettes.

Exchanging cuvettes is carried out as follows: after removing the upper parts of the two contact blocks—this is done by fully unscrewing the four screws 7—the used cuvette is taken out of its seating in the lower part of the contact block and a fresh cuvette is placed in the semicircular apertures of the lower parts in such manner that the annular slots 13 each point downwards and the filling aperture 15 for the analysis sample obtains the correct position for the usually automated filling operation. This necessary adjustment can always be achieved in the cuvette system described which consists of a cuvette tube 11 and clamped contact rings (with or without a slot) since it is exactly the clamping seat which enables a corresponding matching, albeit by turning about or sliding along the cuvette axis (and cuvette surface, respectively).

It is to be noted that the screw connection mentioned in the example of the upper part and the lower part of the contact blocks was chosen only for an experimental construction. For an AAS apparatus which can readily be used in practice a different closing mechanism in which, as already mentioned, resilient forces, mass forces, pneumatically or hydraulically moved contacts or the like are used, is to be preferred since the latter permits a very much more protected and certainly also more rapid exchange of the cuvettes.

Various shapes of AAS cuvettes were tested upon testing the device according to the invention. The electrical energy required for the heating $$E_{el} = N \cdot t_E$$

wherein

N = power in Watt
$t_E$ = switch-on period per pulse was adjusted—for comparison—in all cases at approximately 7.0 to 7.2 kWs. The tests were carried out in pulse operation with $t_E = 8$ s switching-on time (=heating phase) and $t_A = 120$ s off-time (=cooling phase) over each time differently long pulse sequence times. The voltages at the cuvettes were approximately 3.5 to 5.5 Volts, the corresponding electric currents were 250 to 160 A. From this it results, in agreement with the above-mentioned equation, that $$N \cdot t_E = 3.5 \text{ V} \cdot 250 \text{ A} \cdot 8 \text{ s} = 7,000 \text{ W} \cdot \text{s or } 7.0 \text{ kW} \cdot \text{s}$$

$$N \cdot t_E = 5.5 \text{ V} \cdot 160 \text{ A} \cdot 8 \text{ s} = 7,040 \text{ W} \cdot \text{s or } 7.04 \text{ kWs}$$

The cuvette was always in a vacuum (recipient) at a pressure of 1.33 to $2.66 \times 10^{-5}$ mBar. Test durations (pulse repetition times) of 10 hours (approximately 280 load pulses) to 200 hours (approximately 5600 load pulses) were carried out. The highest temperatures measured and corrected by means of optical pyrometers were approximately 2300° C. in the inner space of a cuvette (center), approximately 2000° C. on a cuvette surface (center), approximately 1870° C. on the inner surface of a cuvette surrounded by a contact (cuvette end, inside), and approximately 300° C. in the expansion groove of the contact block.

The expression "corrected" means that the measured temperatures were converted to the real temperatures. The influence of the losses resulting from reflection at and absorption in the glass recipient as well as the emission coefficient of the cuvette were taken into account.

No corrosion or mechanical damage or deformation was observable at the contact faces of the copper blocks used. No disturbance occurred. All test were ended at will.

The self-fixing, i.e. the adjustment of the cuvettes in a defined position, operated perfectly when the graphite foil method was used. When using foils in immediate contact with the metal parts of the device, these parts, after long-term tests, showed a certain "plating-in" of graphite which apparently has a favourable effect as regards corrosion-resistance.

An evaluated calculation of the energy balance in the system described leads to the result that, in accordance with the type of cuvette and arrangement, the delivery of the supplied energy occurs up to 70 to 75% by radiation and up to 25 to 30% by thermal conductivity. In the tests a fan cooling of the solid copper lead-throughs (cross-section approximately 100 mm$^2$) outside the recipient was sufficient to produce a sufficiently low temperature of the metal contacts.

What is claimed is:

1. A heating device for an atomic absorption spectrometer providing electrothermal heating of a sample, said heating device comprising a hollow tubular body for receiving a sample, said tubular body including a radial aperture at a central portion to introduce said sample, said sample being heated by current passage through said tubular body;

a pair of contacts at each end of said tubular body, said pair of contacts including a first lower rigid part and a second upper detachable part, said pair of contacts providing current at each end of said tubular body, an aperture provided by each pair of contacts to hold each end of said tubular body, each said aperture extending partly in said upper part and partly in said lower part of each said pair of contacts, the improvement comprising each aperture having a diameter in a vertical direction shorter than a diameter in a horizontal direction, each upper part of each pair of contacts having a groove extending upwardly and parallel to the longitudinal axis of said tubular body, and means at each said aperture for holding each end of said tubular body.

2. A heating device according to claim 1, wherein said means for holding includes a resilient clamping ring having an inside diameter slightly smaller than the outside diameter of said tubular body, said clamping ring having an outside diameter corresponding to said aperture in each pair of contacts, and said clamping ring having a vertical slot at the area of said lower part of each of said pair of contacts.

3. A heating device according to claim 2, wherein said inside diameter of said clamping ring is 0.4 to 0.5% smaller than said outside diameter of said tubular body.

4. A heating device according to claim 3, wherein said upper part of said pair of contacts has a facing surface in contact with at least a portion of an outside edge of said lower part of said pair of contacts, said facing surface enclosing an angle of approximately 0.14°.

5. A heating device according to claim 1, wherein said means for holding includes flanges at said ends of said tubular body and graphite foil surrounding said flanges.

6. A heating device according to claim 1, wherein said means for holding includes graphite foils at inner surfaces of said aperture at each end of said tubular body.

7. A heating device according to claim 1 or claim 2 or claim 3 or claim 4 or claim 5 or claim 6, wherein said diameter each said aperture in said vertical direction is 0.4 to 0.6% shorter than said diameter in said horizontal direction.

8. A heating device according to claim 1, wherein said inside diameter of said clamping ring is 0.4 to 0.5% smaller than said outside diameter of said tubular body.

9. A heating device according to claim 8, wherein said diameter of each said aperture in said vertical direction is 0.4 to 0.6% shorter than said diameter in said horizontal direction.

10. A heating device according to claim 1, wherein said upper part of said pair of contacts has a facing surface in contact with at least a portion of an outside edge of said lower part of said pair of contacts, said facing surface enclosing an angle of approximately 0.14°.

11. A heating device according to claim 10, wherein said diameter of each said aperture in said vertical direction is 0.4 to 0.6% shorter than said diameter in said horizontal direction.

* * * * *